United States Patent [19]

Chase et al.

[11] 4,307,043
[45] Dec. 22, 1981

[54] METHOD OF ATTACHING RETENTION LOOPS TO AN INTRAOCULAR LENS

[75] Inventors: Charles P. Chase, Brea; Richard B. MacAnally, Altadena, both of Calif.

[73] Assignee: Heyer-Schulte Corporation, Goleta, Calif.

[21] Appl. No.: 186,800

[22] Filed: Sep. 12, 1980

Related U.S. Application Data

[62] Division of Ser. No. 60,529, Jul. 25, 1979, Pat. No. 4,242,761.

[51] Int. Cl.³ .......................................... B29D 11/00
[52] U.S. Cl. .................................... 264/1.7; 264/1.4
[58] Field of Search ................. 264/1.4, 1.7, 2.7, 1.1; 3/13

[56] References Cited

U.S. PATENT DOCUMENTS

| | | | |
|---|---|---|---|
| 3,994,027 | 11/1976 | Jensen et al. | 3/13 |
| 4,012,823 | 3/1977 | Richards | 3/13 |
| 4,150,471 | 4/1979 | Richards et al. | 264/1.7 |
| 4,155,125 | 5/1979 | Woodcock et al. | 3/13 |

Primary Examiner—James B. Lowe
Attorney, Agent, or Firm—Larry N. Barger

[57] ABSTRACT

An optical section of an intraocular lens has a pair of spaced apart threaded recesses which are threadingly locked to threaded shank sections of an iris retention loop. The shank sections are integrally joined to such loop so each shank section acts as an anchor preventing a screwing movement of the other shank relative to the optical section. A method is described of expanding a shank section of a lens retention member in situ within a threaded or other undercut recess of an optical section of an intraocular lens.

8 Claims, 4 Drawing Figures

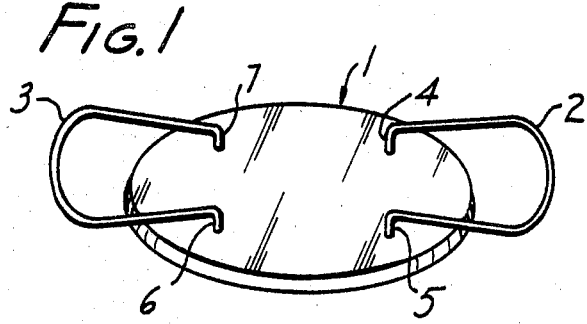
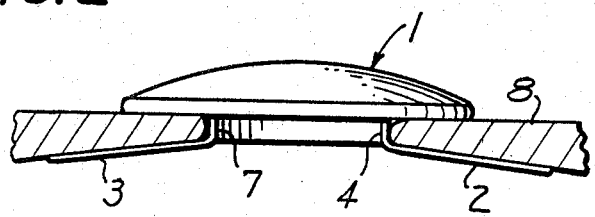
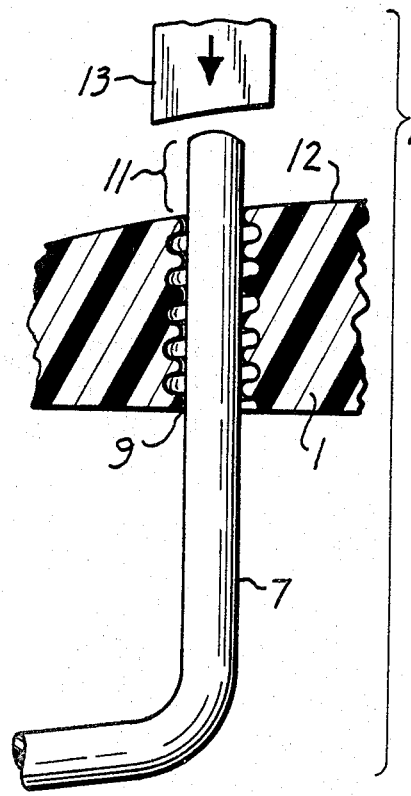
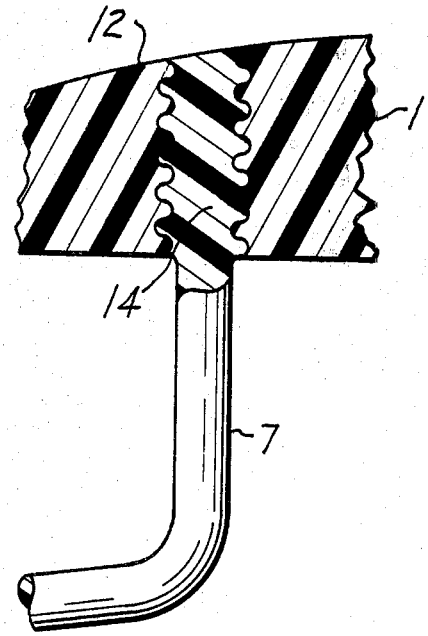

METHOD OF ATTACHING RETENTION LOOPS TO AN INTRAOCULAR LENS

This application is a division of application Ser. No. 060,529, filed July 25, 1979, now U.S. Pat. No. 4,242,761.

BACKGROUND

U.S. Pat. No. 3,996,626 schematically shows how a typical intraocular lens is surgically implanted within the eye. An optical section fits against one face of the iris (often the anterior) and two or more retention loops fit against an opposite face of the iris (often the posterior). Each iris retention loop has a pair of shank sections which are secured to the optical section to provide a space for receiving the iris. It is important to firmly lock the shank sections to the optical section to prevent any change in the length of the shank section.

The above patent describes a process wherein the shank sections are positioned in passages of the optical section so that a portion of the shank sections protrude beyond a forward surface of the optical sections. Enlarged bulbular portions are formed on such protrusions. The bulbular portions are then driven into the passages of the optical section with a vibrating punch to cause the lens to distort outwardly within a central portion of the passage to "cold flow" and form a pocket for the bulbular portion. Such "cold flow" could stress the optical section and change its optical properties.

Another approach to maintaining a precise length of the shank sections for receiving the iris is described in U.S. Pat. No. 3,991,426. Here a series of small individual screws are secured to the optical section and pointed heads of the screw pierce the iris. A separate snap-on ring fits over the protruding heads of the screws to act as a retainer and thereby replace the conventional iris loops that are integral with their shank sections. In addition to requiring complicated special tools for use during the steps of piercing the iris and assembling the snap ring, the individual screws could possibly twist within the snap ring to loosen and increase the space in which the iris fits.

Retention loops of a special material, such as Supramid (a Nylon type material), have been heated and forced into a conical recess in the optical section in U.S. Pat. No. 3,994,026. The optical section of an intraocular lens is usually made of polymethylmethacrylate (PMMA). The machined conical recess of this patent would have some surface roughness formed during the machining step which would have a slight clinging effect on the Supramid shank section. In practice, such design has limited holding power and the shank section could be pulled out of this conical recess with a small force. Because of the dissimilarity of materials, there is little, if any, fusion bond between the shank section and the optical section, particularly since the optical section is not heated to its softening point. Such high temperature heating would alter the optical properties of previously ground or molded and polished optical sections.

SUMMARY OF THE INVENTION

The present invention overcomes the problems of the above prior art by providing a pair of spaced threaded recesses in the optical section into each of which is inserted a generally cylindrical nonthreaded shank section of an iris loop. Energy, such as heat and/or pressure, applied to the shank section causes a thread to form in situ and lock to the optical section of the lens. Thus, no threading or twisting motion is needed on the shank sections to assemble them to the optical section. Also, because there are two shank sections integrally joined to the loop, each shank section acts as a locking anchor preventing the other shank section from unscrewing. A method is described in which a rod-like shank section is moved into a recess of the optical section which has an undercut recess (such as a thread) and such shank section is expanded in situ.

THE DRAWINGS

FIG. 1 is a rear prospective view of a typical intraocular lens;

FIG. 2 is a side view of the intraocular lens shown attached to the iris of an eye;

FIG. 3 is an enlarged sectional view showing a shank section of an iris retention loop in the process of attaching it to an optical section of the lens; and FIG. 4 is an enlarged sectional view showing a shank section of the iris retention loop after it has been attached to an optical section of the lens.

DETAILED DESCRIPTION

The rear prospective view of FIG. 1 shows an intraocular lens with an optical section shown generally as 1. To this optical section is attached iris retention loops 2 and 3 that are secured to the optical section by shank sections 4, 5, 6, and 7. The intraocular lens of FIG. 1 is intended to be representative of many types of lenses, including different rod-like iris retention means.

In FIG. 2, the intraocular lens is secured to an iris 8 of an eye. Typically, the optical section 1 is in an anterior section of the eye and rests against a forward or anterior face of the iris 8. The iris retention loops 2 and 3 fit against a rear or posterior face of iris 8. It can be seen that shank sections 4 and 7 are very critical in controlling the spacing into which the iris 8 fits.

In FIG. 3, the optical section 1 has a drilled recess 9 that can be of a diameter of 0.004 to 0.020 inch (0.10 to 0.51 mm). A hole diameter of 0.008 inch (0.20 mm) extending completely through the optical section has worked very well. This hole is then tapped with microthreads. A tap of 0.30 UNM (Unified National Minature) size can be used. Different thread pitches could be used in the range of 100 to 300 threads/inch (3.9 to 12 threads/mm) with 200 threads/inch (7.9 threads/mm) working very well. It is understood that the diameter, thread pitch, and thread depth could be varied without departing from the spirit and scope of the invention. Also, other forms of specially formed undercuts could be used besides threads in the method of practicing this invention. Threads, however, are the most convenient to form.

In FIG. 3, the shank section 7 is formed and placed in proper jigging to insure a precisely controlled length of a tip section 11 that protrudes from a forward face 12 of the optical section of the lens. When properly jigged to the position shown in FIG. 3, energy in the form of heat and/or pressure is applied to the shank section to laterally expand a portion of shank section 7 within the threaded bore 9 of the optical section. A tool for applying such energy is schematically shown at 13 and has a face generally following the contour of the optical section's front surface. It is understood that heat can be applied in many forms, such as conductive, ultrasonic, etc., with the important aspect being to soften the shank section so it expands. Some forms of heat application may not require the schematically shown tool 13.

Because of the precisely controlled protruding length 11 of shank 7 and the expansion of a locking portion 14 of shank section 7, the protruding portion 11 disappears after the expansion step as shown in FIG. 4. This provides a very smooth forward surface 12 at the inner face between shank section 7 and ocular section 1. This smooth forward section is important for intraocular lenses that fit within the eye.

The method of the present invention is much simpler than previous methods of attaching iris retention loops to optical sections of intraocular lenses. The forming in situ process avoids the problem of manually screwing a threaded member in too far or not far enough to change the spacing between the optical section and iris loops. This process also eliminates the requirement for adhesives or other extraneous materials. Also, in the preferred version of the invention, two shanks are integrally connected to a loop section, and each shank acts as an anchor preventing the twisting unscrewing motion of the other shank.

The intraocular lens structure and method of this invention work very well when the optical section is of a polymethylmethacrylate (PMMA) and the iris loops and integral shank sections are of an inert thermoplastic material, such as polypropylene. In the past, it has been extremely difficult to adhesively bond or otherwise firmly secure the polypropylene shank to an optical section. This is because of the slipperiness and nonadhering characteristics of polypropylene. However, polypropylene is desired for intraocular lens retention loops because of its inertness, biocompatibility, and stiffness. It is preferred over the previous metal loops of platinum-iridium wire.

In the foregoing specification, a specific example has been used to describe the invention. However, it is understood that certain modifications can be made to this example by those skilled in the art without departing from the spirit and scope of this invention.

We claim:

1. A method of making an intraocular lens comprising the steps of:
    (a) forming an optical section with a recess having at least one substantially enlarged undercut section;
    (b) forming a retention member having at least one integral rod-like shank section;
    (c) inserting the shank section of the retention member into the recess;
    (d) applying energy in the form selected from the group consisting of heat, pressure, and a combination thereof to the shank section until the shank section permanently expands in situ to create at least one substantially enlarged lateral protrusion fitting in the enlarged undercut section locking the retention member to the optical section.

2. A method as set forth in claim 1, wherein there are a series of enlarged undercut sections in the recess of the optical section into which the shank is expanded.

3. A method as set forth in claim 2, wherein the recess is threadingly tapped to form spiral threads with undercut sections in the recess.

4. A method as set forth in claim 1, wherein the recess is formed to extend completely through the optical section.

5. A method as set forth in claim 1, wherein the optical section is formed with a pair of spaced apart recesses, each having an enlarged undercut section; and the retention member is formed with a loop integrally connected to spaced apart shank sections; and the method includes inserting and expanding shank sections in each recess.

6. A method as set forth in claim 1, wherein the recess is an opening extending completely through the optical section; and the method includes the step of forming the rod-like shank with a predetermined excess length; inserting the shank into the opening from one surface of the optical section so an end portion of the shank section protrudes a predetermined distance from an opposite surface of the optical section; and applying the deforming energy to the shank section.

7. A method as set forth in claim 6, wherein the excess length of the shank section is selected to provide a smooth flush surface blending with the opposite surface of the optical section upon expansion of the shank section.

8. A method as set forth in claim 6, wherein the energy is applied with a tool conforming generally to the geometry of said opposite surface of the optical section.

* * * * *